US012573499B2

(12) United States Patent
Hatsutani

(10) Patent No.: US 12,573,499 B2
(45) Date of Patent: Mar. 10, 2026

(54) TRAINING DATA GENERATION DEVICE, TRAINING DATA GENERATION METHOD AND PROGRAM, AND LEARNING DEVICE

(71) Applicant: FUJIFILM Corporation, Tokyo (JP)

(72) Inventor: Taro Hatsutani, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 275 days.

(21) Appl. No.: 18/474,248

(22) Filed: Sep. 26, 2023

(65) Prior Publication Data

US 2024/0021294 A1     Jan. 18, 2024

Related U.S. Application Data

(63) Continuation of application No. PCT/JP2022/011462, filed on Mar. 15, 2022.

(30) Foreign Application Priority Data

Apr. 1, 2021    (JP) ................................. 2021-063024

(51) Int. Cl.
*G06K 9/00*          (2022.01)
*G06V 10/82*          (2022.01)
          (Continued)

(52) U.S. Cl.
CPC ............. *G16H 30/40* (2018.01); *G06V 10/82* (2022.01); *G06V 20/70* (2022.01)

(58) Field of Classification Search
CPC ........ G16H 30/40; G16H 50/20; G16H 50/70; G06V 10/82; G06V 20/70; G06V 10/7753; G06V 2201/03; A61B 5/00; G06N 20/00
See application file for complete search history.

(56) References Cited

U.S. PATENT DOCUMENTS

2020/0134427 A1    4/2020    Oh et al.
2021/0158101 A1    5/2021    Shinzaki et al.

FOREIGN PATENT DOCUMENTS

CN          112183577 A  *  1/2021  ........... G06F 18/214
JP          2010028486        2/2010
          (Continued)

OTHER PUBLICATIONS

Munetaka Minoguchi et al., "Weakly Supervised Dataset Collection for Robust Person Detection", retrieved from arXiv database, arXiv:2003.12263v2 [cs.CV], May 1, 2020, pp. 1-10.
          (Continued)

*Primary Examiner* — Xin Jia
(74) *Attorney, Agent, or Firm* — JCIPRNET

(57) ABSTRACT

There are provided a training data generation device, a training data generation method, and a learning device. First images having no label and first texts attached to the first images having no label are acquired, first information on at least one of a region, a type, or a state of the first image having no label is acquired from the first image having no label, second information on at least one of a region, a type, or a state of the first image having no label is acquired from the first text, an output of a first learning model to which the first images having no label are input is acquired as first pseudo-labels of the first images having no label, and the first pseudo-labels are filtered on the basis of the first information and the second information.

8 Claims, 6 Drawing Sheets

(51) Int. Cl.
    *G06V 20/70*     (2022.01)
    *G16H 30/40*     (2018.01)

(56)             References Cited

FOREIGN PATENT DOCUMENTS

| JP | 2020008905 | 1/2020 | |
| JP | 2020036837 | 3/2020 | |
| JP | 2020101968 | 7/2020 | |
| JP | 2021089491 | 6/2021 | |
| WO | WO-2019237191 A1 * | 12/2019 | ........... A61B 5/0084 |

OTHER PUBLICATIONS

Kunpeng Li et al., "Visual Semantic Reasoning for Image-Text Matching", 2019 IEEE/CVF International Conference on Computer Vision (ICCV), Oct. 27-Nov. 2, 2019, pp. 4654-4662.
"International Search Report (Form PCT/ISA/210) of PCT/JP2022/011462", mailed on May 31, 2022, with English translation thereof, pp. 1-5.
"Written Opinion of the International Searching Authority (Form PCT/ISA/237) of PCT/ JP2022/011462", mailed on May 31, 2022, with English translation thereof, pp. 1-10.

* cited by examiner

FIG. 2

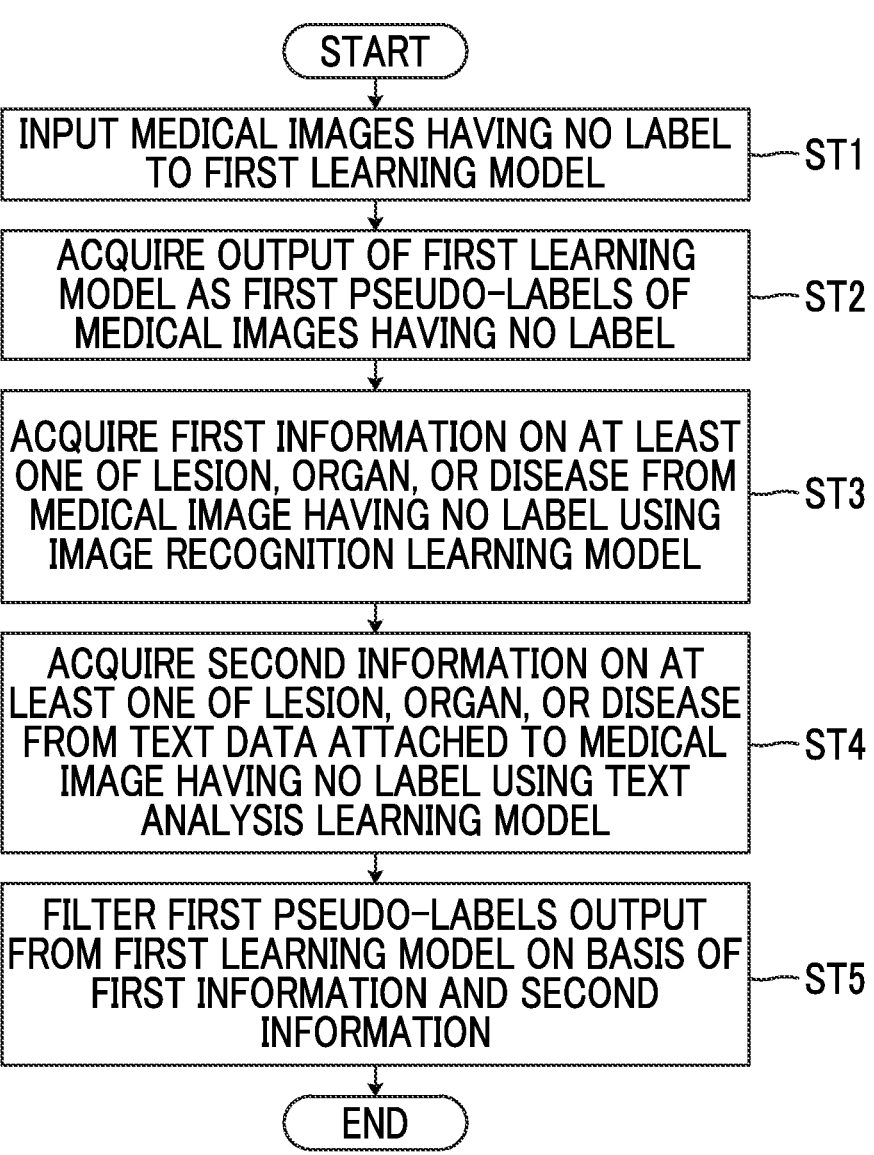

START

INPUT MEDICAL IMAGES HAVING NO LABEL TO FIRST LEARNING MODEL — ST1

ACQUIRE OUTPUT OF FIRST LEARNING MODEL AS FIRST PSEUDO-LABELS OF MEDICAL IMAGES HAVING NO LABEL — ST2

ACQUIRE FIRST INFORMATION ON AT LEAST ONE OF LESION, ORGAN, OR DISEASE FROM MEDICAL IMAGE HAVING NO LABEL USING IMAGE RECOGNITION LEARNING MODEL — ST3

ACQUIRE SECOND INFORMATION ON AT LEAST ONE OF LESION, ORGAN, OR DISEASE FROM TEXT DATA ATTACHED TO MEDICAL IMAGE HAVING NO LABEL USING TEXT ANALYSIS LEARNING MODEL — ST4

FILTER FIRST PSEUDO-LABELS OUTPUT FROM FIRST LEARNING MODEL ON BASIS OF FIRST INFORMATION AND SECOND INFORMATION — ST5

END

TRAINING DATA GENERATION DEVICE, TRAINING DATA GENERATION METHOD AND PROGRAM, AND LEARNING DEVICE

CROSS-REFERENCE TO RELATED APPLICATIONS

The present application is a Continuation of PCT International Application No. PCT/JP2022/011462 filed on Mar. 15, 2022 claiming priority under 35 U.S.C § 119(a) to Japanese Patent Application No. 2021-063024 filed on Apr. 1, 2021. Each of the above applications is hereby expressly incorporated by reference, in its entirety, into the present application.

BACKGROUND OF THE INVENTION

1. Field of the Invention

The present invention relates to a training data generation device, a training data generation method, a training data generation program, and a learning device, and more particularly to a technique that generates training data with high accuracy.

2. Description of the Related Art

It is known that the number of data greatly affects performance in the training of a deep neural network. There are some large-scale datasets, such as ImageNet and MS COCO, but there are also fields in which sufficient data do not exist, such as a medical field. US2020/0134427A discloses a method using a pseudo-label as one of countermeasures in a case where the amount of data is small. Specifically, data having no label are input to a model that is trained using data having labels, and the model is trained again using data having labels and data having no label while an output of the model is used as a pseudo-label.

However, since the output is not filtered in the technique disclosed in US2020/0134427A, a lot of noise is generated in the output depending on the performance of the model that is trained using data having labels. For this reason, there is a possibility that the quality of the pseudo-label may deteriorate.

On the other hand, Weakly Supervised Dataset Collection for Robust Person Detection/Munetaka Minoguchi, Ken Okayama, Yutaka Satoh, Hirokatsu Kataoka National Institute of Advanced Industrial Science and Technology (AIST) Tsukuba, Ibaraki, Japan (https://arxiv.org/pdf/ 2003.12263.pdf) discloses a technique for filtering an output result using a support vector machine (SVM).

SUMMARY OF THE INVENTION

However, the technique disclosed in Weakly Supervised Dataset Collection for Robust Person Detection/Munetaka Minoguchi, Ken Okayama, Yutaka Satoh, Hirokatsu Kataoka National Institute of Advanced Industrial Science and Technology (AIST) Tsukuba, Ibaraki, Japan (https:// arxiv.org/pdf/2003.12263.pdf) has a drawback that a trained SVM is required.

The present invention has been made in consideration of the above-mentioned circumstances, and an object of the present invention is to provide a training data generation device, a training data generation method, a training data generation program, and a learning device that generate training data used to improve the performance of a learning model.

A training data generation device according to an aspect of the present invention comprises at least one processor, and at least one memory that stores a command to be executed by the at least one processor. The at least one processor acquires first images having no label and first texts attached to the first images having no label, acquires first information on at least one of a region, a type, or a state of a subject of the first image having no label from the first image having no label, acquires second information on at least one of a region, a type, or a state of the subject of the first image having no label from the first text, inputs the first images having no label to a first learning model, which outputs a label relating to a region-of-interest of an image in a case where the image is input, and acquires an output of the first learning model as first pseudo-labels of the first images having no label, and filters the first pseudo-labels on the basis of the first information and the second information. According to this aspect, it is possible to generate training data that are used to improve the performance of the learning model.

It is preferable that the first image having no label is a medical image, and the region, the type, and the state of the subject are a position of a lesion, an organ name, and a disease name, respectively. This aspect is suitable for a medical image, and the first pseudo-labels can be filtered on the basis of information on the position of the lesion, the organ name, and the disease name.

It is preferable that the at least one processor inputs the first image having no label to an image recognition learning model, which outputs information on at least one of the region, the type, or the state of the subject of the image from the image in a case where the image is input, and acquires the first information. Further, it is preferable that the at least one processor inputs the first text to a text analysis learning model, which outputs information on at least one of a region, a type, or a state from a text in a case where the text is input, and acquires the second information. Since the learning model is used, the first information and the second information can be appropriately acquired.

It is preferable that the at least one processor deletes the first pseudo-labels different from at least one of the first information or the second information. Accordingly, it is possible to make only the first pseudo-labels, which match the first information and the second information, remain.

A learning device according to another aspect of the present invention comprises the training data generation device. It is preferable that the at least one processor trains the first learning model using an image having a label and a label of the image having a label as training data, and trains a second learning model, which outputs a label relating to a region-of-interest of the image in a case where the image is input, using the first image having no label and a first label that is the first pseudo-label having been subjected to the filtering as training data. According to this aspect, it is possible to improve the performance of the learning model.

It is preferable that the first learning model and the second learning model include convolutional neural networks. Further, it is preferable that the first learning model and the second learning model include convolutional neural networks having the same configuration. According to this aspect, it is possible to improve the performance of the convolutional neural network.

It is preferable that, in a case where an initial value of M as a variable is set to 1 and N is an integer of 2 or more, the at least one processor repeats processing the N times. The processing includes: acquiring M-th images having no label and M-th texts attached to the M-th images having no label; acquiring the first information of the M-th image having no label on at least one of a region, a type, or a state of a subject of the M-th image having no label from the M-th image having no label; acquiring the second information of the M-th image having no label on at least one of a region, a type, or a state of the subject of the M-th image having no label from the M-th text; inputting the M-th images having no label to a M-th learning model and acquires an output of the M-th learning model as the M-th pseudo-labels of the M-th images having no label; filtering the M-th pseudo-labels on the basis of the first information and the second information of the M-th image having no label; training a (M+1)-th learning model, which outputs a label relating to a region-of-interest of the image in a case where the image is input, using the M-th image having no label and the M-th pseudo-label having been subjected to the filtering as training data; and adding 1 to the M. Accordingly, it is possible to sequentially generate learning models of which the performance is improved.

A training data generation method according to another aspect of the present invention comprises: an image acquisition step of acquiring first images having no label and first texts attached to the first images having no label; a first information acquisition step of acquiring first information on at least one of a region, a type, or a state of a subject of the first image having no label from the first image having no label; a second information acquisition step of acquiring second information on at least one of a region, a type, or a state of the subject of the first image having no label from the first text; a pseudo-label acquisition step of inputting the first images having no label to a first learning model, which outputs a label relating to a region-of-interest of an image in a case where the image is input, and acquiring an output of the first learning model as first pseudo-labels of the first images having no label; and a filtering step of filtering the first pseudo-labels on the basis of the first information and the second information. According to this aspect, it is possible to generate training data that are used to improve the performance of the learning model.

A program according to another aspect of the present invention is a program that causes a computer to execute the training data generation method. A computer-readable non-transitory storage medium on which the program is recorded may also be included in this aspect.

According to the present invention, it is possible to generate training data that are used to improve the performance of the learning model.

BRIEF DESCRIPTION OF THE DRAWINGS

FIG. 2 is a flowchart showing the respective steps of a training data generation method.

4

DESCRIPTION OF THE PREFERRED
EMBODIMENTS

Figure 1:
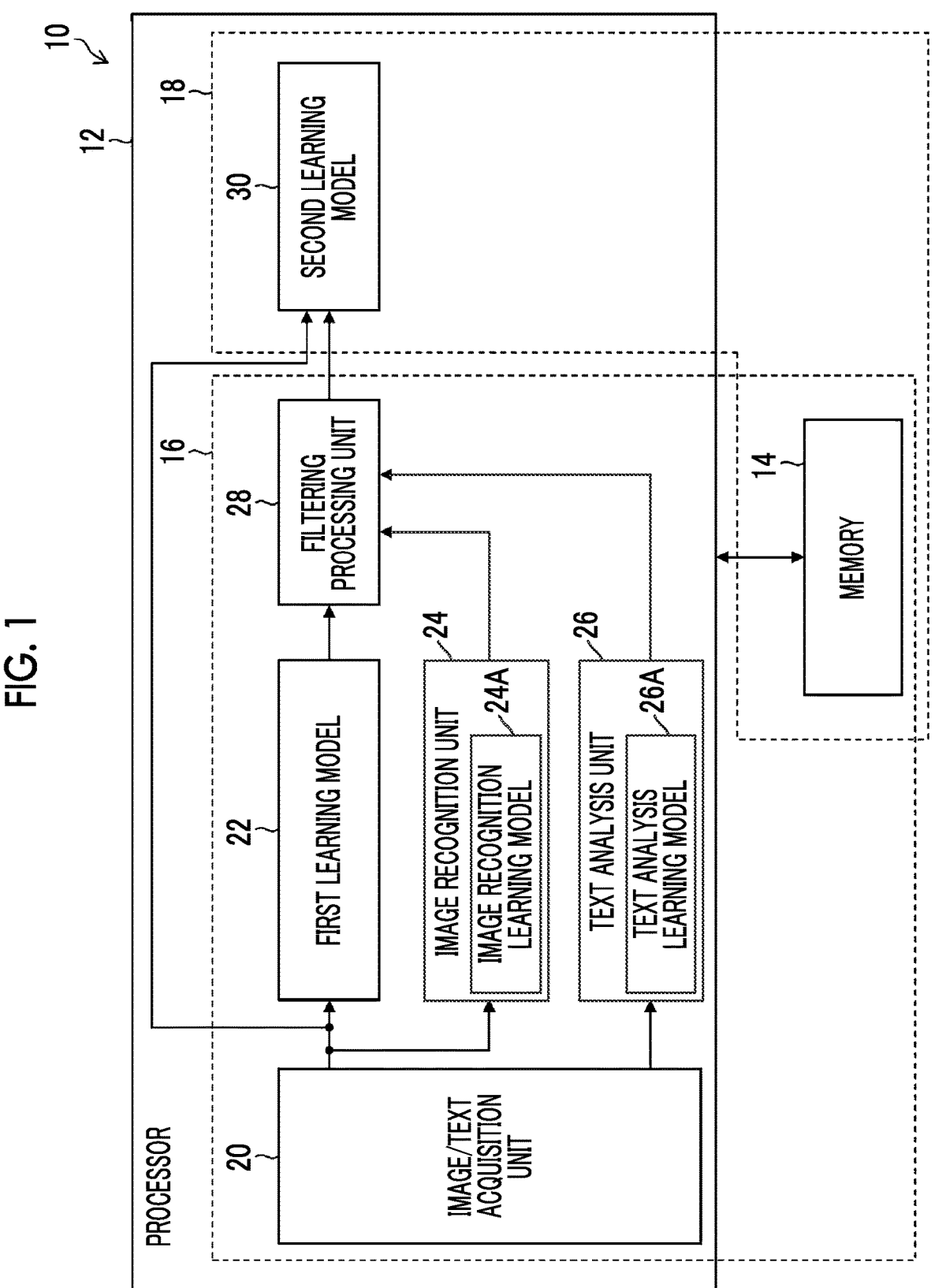
FIG. 1 is a block diagram of an information processing apparatus according to the present embodiment.

Preferred embodiments of the present invention will be described in detail below with reference to the accompanying drawings.
[Overall Configuration of Information Processing Apparatus]
FIG. 1 is a block diagram of an information processing apparatus 10. The information processing apparatus 10 generates training data that is used to train a learning model for detecting an object from an image. In addition, the information processing apparatus 10 trains the learning model using the training data. Here, an example of a learning model for extracting a lesion region from a medical image will be described. As shown in FIG. 1, the information processing apparatus 10 includes a processor 12 and a memory 14.

The processor 12 executes a command stored in the memory 14. A hardware structure of the processor 12 is various processors to be described below. Various processors include a central processing unit (CPU) that is a general-purpose processor acting as various functional units by executing software (program), a graphics processing unit (GPU) that is a processor specialized in image processing, a programmable logic device (PLD) that is a processor of which the circuit configuration can be changed after manufacture, such as a field programmable gate array (FPGA), a dedicated electrical circuit that is a processor having circuit configuration specifically designed to perform specific processing, such as an application specific integrated circuit (ASIC), and the like.

One processing unit may be formed of one of these various processors, or may be formed of two or more processors of the same type or different types (for example, a plurality of FPGAs, a combination of a CPU and an FPGA, or a combination of a CPU and a GPU). Further, a plurality of functional units may be formed of one processor. As examples in which a plurality of functional units are formed of one processor, first, there is an aspect in which one processor is formed of a combination of one or more CPUs and software as typified by a computer, such as a client or a server, and acts as a plurality of functional units. Second, there is an aspect in which a processor fulfilling the functions of the entire system, which includes a plurality of functional units, with one integrated circuit (IC) chip as typified by System On Chip (SoC) or the like is used. In this way, various functional units are formed using one or more of the above-mentioned various processors as hardware structures.

In addition, the hardware structures of these various processors are more specifically electrical circuitry in which circuit elements, such as semiconductor elements, are combined.

The memory 14 stores a command that is to be executed by the processor 12. The memory 14 includes a random access memory (RAM) and a read only memory (ROM) (which are not shown). The processor 12 uses the RAM as a work area; executes software using various programs, which include a training data generation method, and parameters stored in the ROM; and performs various types of processing of the information processing apparatus 10 using the parameters stored in the ROM or the like.
[Functional Configuration of Information Processing Apparatus]
As shown in FIG. 1, the information processing apparatus 10 includes a training data generation device 16 and a learning device 18. Functions of the training data generation device 16 and the learning device 18 are realized by the processor 12.

The training data generation device 16 comprises an image/text acquisition unit 20, a first learning model 22, an image recognition unit 24, a text analysis unit 26, and a filtering processing unit 28.

The image/text acquisition unit 20 acquires medical images and image reading reports that are attached to the medical images. The medical image is an image that is captured by a medical imaging device, such as an X-ray imaging device, a computed tomography (CT) device, a magnetic resonance imaging (MRI) device, a positron emission tomography (PET) device, an ultrasound device, or a computed radiography (CR) device using a planar X-ray detector. The image reading report is a report that is made by a radiologist after the radiologist reads the medical image, and includes a doctor's note (an example of "text") that is sentence information in which information on at least one of a lesion, an organ, or a disease of a subject in the medical image is described. Here, information on the lesion is information on a position at which the lesion occurs (the position of the lesion). The position of the lesion is coordinate information associated with a specific region that is included in one organ. For example, in a case where the organ is the brain, the position of the lesion is coordinate information associated with each of portions that are included in the brain, such as the frontal lobe, the right frontal lobe, the cerebrum, and the cerebellum, a region that is included in each of the portions, or each portion and each region. Information on the organ is information indicating the name of an organ at which the lesion occurs, and is, for example, the brain, the heart, the lung, and the like. Information on the disease is information indicating the name or type of a disease that causes the lesion, and is, for example, cerebral infarction, myocardial infarction, pneumonia, a tumor, a tubercle, and the like.

Medical images to which correct answer labels are given (images having labels) and medical images to which correct answer labels are not given (images having no label) are included in the medical images that are acquired by the image/text acquisition unit 20. The correct answer label will be described later.

The first learning model 22 is a machine learning model that outputs a label relating to a region-of-interest of an input image in a case where the image is input. The first learning model 22 may be a trained model. The first learning model 22 is formed of, for example, a convolutional neural network (CNN). The first learning model 22 is trained using a pair (correct answer data set) of a teacher image and a correct answer label that includes information on a lesion in the teacher image. The correct answer label is manually made, and includes, for example, information on at least any one of a position at which the lesion is present (the position of the lesion) in the teacher image, the name or type of an organ at which the lesion occurs, or information that indicates the name or type of a disease causing the lesion. Information on the position of the lesion may be the coordinate information of the lesion in the image, or may be information indicating a specific region in which the lesion is present among a plurality of regions preset for each organ. The correct answer label to be given is accurate, but it is difficult to align a lot of images having correct answer labels. For this reason, the first learning model 22 has relatively low accuracy since being trained using a relatively small amount of training data.

The medical images acquired by the image/text acquisition unit 20 are input to the first learning model 22. The first learning model 22 outputs labels that relate to lesion regions of the input medical images. The labels, which are output from the first learning model 22, are input to the filtering processing unit 28 to be described later as first pseudo-labels. The label relating to the lesion region includes information on at least any one of the position at which the lesion is present (the position of the lesion) in the image, the name or type of an organ at which the lesion occurs, or the name or type of a disease causing the lesion. The information on the position of the lesion may be the coordinate information of the lesion in the image or may be information indicating a specific region in which the lesion is present among a plurality of regions preset for each organ, as with the above-mentioned information.

In a case where an image is input, the image recognition unit 24 acquires first information on at least one of a region, a type, or a state of a subject on the basis of the input image. Information on the region is information on the position at which the lesion is present (the position of the lesion) in the image. Information on the type is information that indicates the name or type of an organ at which the lesion occurs. Information on the state is information that indicates the name or type of a disease causing the lesion.

Here, the image recognition unit 24 comprises an image recognition learning model 24A. The image recognition learning model 24A is a learning model that outputs the first information on at least one of the position of the lesion, an organ name, or a disease name on the basis of an input medical image in a case where the medical image is input. The image recognition learning model 24A is formed of, for example, a convolutional neural network.

The image recognition unit 24 may acquire the first information using a publicly known technique that is disclosed in JP1995-323024A (JP-H07-323024) and JP1995-031591A (JP-H07-031591).

In a case where a text of the image reading report is input, the text analysis unit 26 acquires second information on at least one of a region, a type, or a state from the input text. The region, type, and state of the second information are the same as the region, type, and state of the first information. That is, information on the region is information on the position of the lesion. Further, information on the type is information that indicates the name or type of an organ at which the lesion occurs. Information on the state is information that indicates the name or type of a disease causing the lesion. The text may be a sentence, or may be a structured enumeration of words. The text may be tag information of an image. Here, the text analysis unit 26 comprises a text analysis learning model 26A. In a case where a text is input, the text analysis learning model 26A acquires the second information on at least one of the position of the lesion, an organ name, or a disease name from the text. The text analysis learning model 26A is formed of, for example, a neural network.

The text analysis unit 26 may acquire the second information from the input text using a dictionary, or may acquire the second information from the input text according to an If-Then rule. Further, the text analysis unit 26 may acquire the second information from the input text using a technique to which publicly known morphological analysis is applied and which is disclosed in JP2013-200592A and JP2012-63919A.

The filtering processing unit 28 acquires the labels, which are output from the first learning model 22, as the first pseudo-labels. Further, the filtering processing unit 28 acquires the first information from the image recognition unit 24. Furthermore, the filtering processing unit 28 acquires the second information from the text analysis unit 26. In addition, the filtering processing unit 28 filters the first pseudo-labels on the basis of the first information and the second information. For example, the filtering processing unit 28 deletes the first pseudo-labels that are different from at least one of the first information or the second information, or information that is included in the first pseudo-labels. In this way, the filtering processing unit 28 performs filtering processing on the first pseudo-labels to generate a first label. That is, the first label is a pseudo-label that have been subjected to the filtering by the filtering processing unit 28 among the first pseudo-labels that are output from the first learning model 22. The first label is a pseudo-label having accuracy higher than the first pseudo-labels.

Further, the learning device 18 comprises a second learning model 30. The second learning model 30 is a machine learning model that outputs a label relating to a region-of-interest of an image in a case where the image is input. The second learning model 30 is formed of, for example, a convolutional neural network. The second learning model 30 may be a convolutional neural network having the same configuration as the first learning model 22. The learning device 18 inputs a correct answer data set to the second learning model 30 and trains the second learning model 30. Furthermore, the learning device 18 inputs a training data set, which is formed of the medical image having no label acquired by the image/text acquisition unit 20 and the first label, to the second learning model 30 and trains the second learning model 30.

For example, the learning device 18 comprises a loss value calculation unit (not shown) and a parameter controller (not shown). The learning device 18 calculates a loss value between a pseudo-label (second pseudo-label) that is output from the second learning model 30 in a case where the medical image having no label of the training data set is input and the first label of the training data set. Further, the learning device 18 adjusts parameters of the second learning model 30 to maximize a similarity between the second pseudo-label output from the second learning model 30 and a label of correct answer data using a backpropagation method on the basis of the calculated loss value.

First Embodiment: Training Data Generation Method

Figure 3:
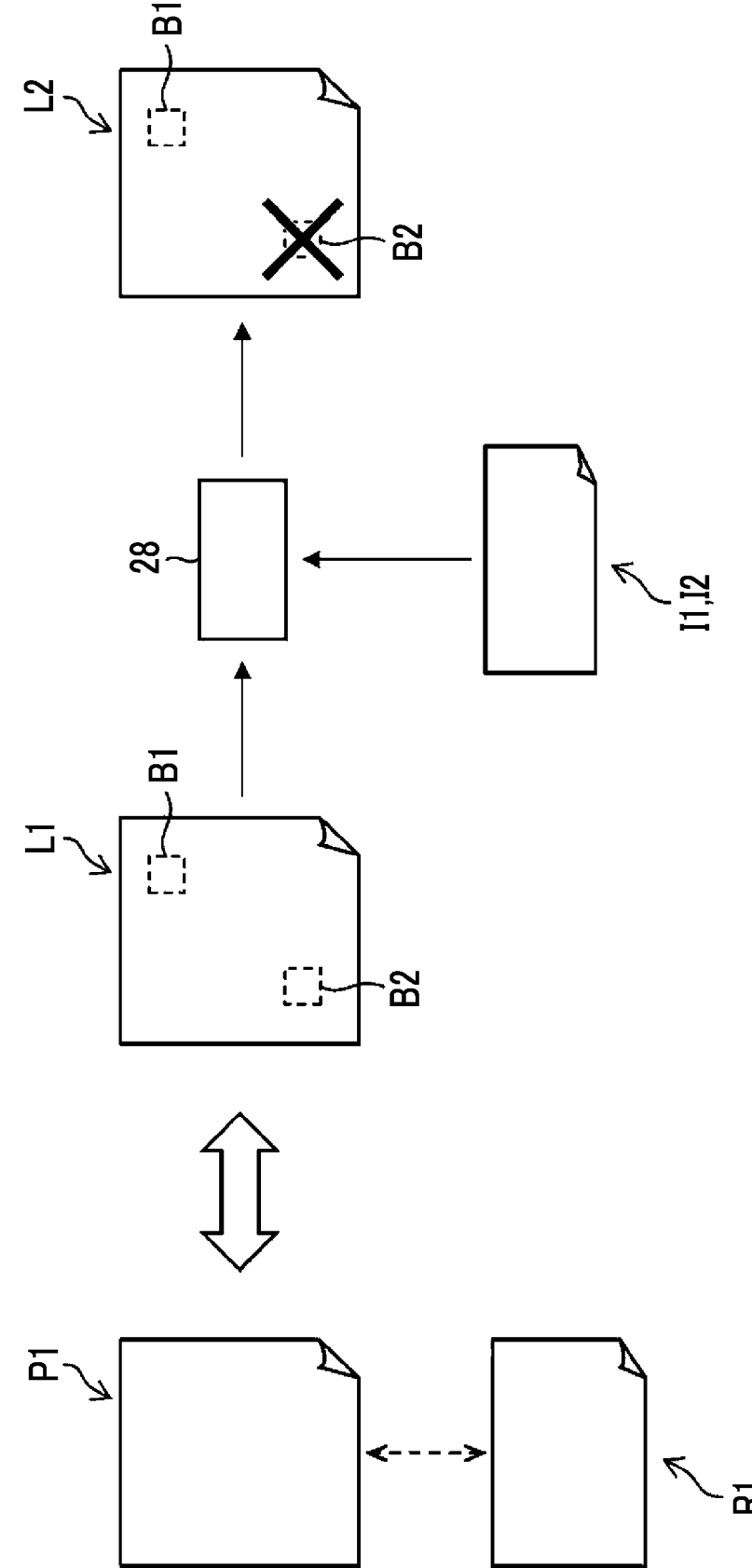
FIG. 3 is a diagram showing data processing of the training data generation method.

FIG. 2 is a flowchart showing the respective steps of a training data generation method that is performed by the information processing apparatus 10. Further, FIG. 3 is a diagram showing data processing of the training data generation method. The training data generation method is realized in a case where the processor 12 executes a training data generation program stored in the memory 14. The training data generation program may be provided by a computer-readable non-transitory storage medium. In this case, the information processing apparatus 10 may read the training data generation program from the non-transitory storage medium and stores the training data generation program in the memory 14.

In Step ST1, the image/text acquisition unit 20 acquires medical images via an input interface (not shown) (an example of "image acquisition step"). Here, the image/text acquisition unit 20 acquires CT images having no label (an example of "first image having no label") and image reading reports that are attached to the CT images having no label. The CT image having no label is an image which is captured by a CT device and in which a label, such as a bounding box, is not given to a region-of-interest. Further, the image reading report includes a text (an example of "first text").

Further, in Step ST1, the image/text acquisition unit 20 inputs the acquired CT images having no label to the first learning model 22 and the image recognition unit 24. Furthermore, the image/text acquisition unit 20 inputs the texts of the acquired image reading reports to the text analysis unit 26.

In Step ST2, the first learning model 22 outputs bounding boxes to the positions of lesion regions of the input CT images having no label. Specifically, the first learning model 22 outputs text information, which is described in the bounding boxes, in association with the position information of the lesions in the CT images having no label. The first learning model 22 may average an output and further stabilize the output by performing data augmentation (test-time-augmentation) on an input, or may increase sensitivity by increasing the number of pseudo-labels. In Step ST2, the filtering processing unit 28 acquires the bounding boxes, which are output from the first learning model 22, as first pseudo-labels of the CT images having no label (an example of "first pseudo-label acquisition step").

FIG. 3 shows a CT image P1 that is the CT image having no label, an image reading report R1 that is attached to the CT image P1, and a first pseudo-label L1 that is output from the first learning model 22. The CT image P1 is an image that is used by the information processing apparatus 10 to generate training data. The image reading report R1 is a report that is made by a radiologist after the radiologist reads the CT image P1, and is stored in association with the CT image P1.

The first pseudo-label L1 is an output of the first learning model 22 to which the CT image P1 is input. Here, the first pseudo-label L1 includes a bounding box B1 and a bounding box B2. The first pseudo-label L1 has only to include position information of each of the bounding box B1 and the bounding box B2 on the CT image P1, and does not need to include image information of the CT image P1.

Returning to the description of FIG. 2, in Step ST3, the image recognition unit 24 inputs the CT image P1 to the image recognition learning model 24A and acquires first information on at least one of the position of the lesion, an organ name, or a disease name from the CT image P1 (an example of "first information acquisition step"). In other words, the image recognition unit 24 acquires information on at least one of a coordinate position or a region where the lesion is present, the name of an organ at which the lesion is present, or the name of a disease that causes the lesion, from the CT image P1.

In Step ST4, the text analysis unit 26 inputs a text of the image reading report R1 to the text analysis learning model 26A, and acquires second information on at least one of the position of the lesion in the CT image P1, the name of the organ, or the name of the disease from the text (an example of "second information acquisition step").

In Step ST5, the filtering processing unit 28 filters the first pseudo-labels acquired in Step ST2 on the basis of the first information acquired in Step ST3 and the second information acquired in Step ST4, and acquires a first label that is the first pseudo-label having been subjected to the filtering (an example of "filtering step"). Specifically, the filtering processing unit 28 compares the first information and the second information with information included in the first pseudo-labels, and deletes the first pseudo-labels or deletes information on the bounding boxes included in the first pseudo-labels in a case where there is information not matching. The first pseudo-label or the information on the bounding box, which remains without being deleted, is the first label. For example, the filtering processing unit 28 deletes the pseudo-labels or the information on the bounding boxes, which are given to impossible regions, as a result of considering the first information or the second information.

The filtering processing unit 28 may filter the first pseudo-labels on the basis of at least one of the first information or the second information. The filtering processing unit 28 may filter the first pseudo-labels according to a confidence degree of the first learning model 22 (an output value of the first learning model 22) in addition to the first information and the second information. The filtering mentioned here is based on a rule. Further, in a case where an object to be inspected is limited to a specific organ, the filtering processing unit 28 may filter the first pseudo-labels depending on an organ name so that information on the bounding boxes other than the bounding box of the specific organ is excluded. In addition, in a case where a lesion is detected outside a body (in a case where a bounding box is given outside the body), the filtering processing unit 28 may filter the first pseudo-labels so that the bounding box given outside the body is excluded.

The filtering processing unit 28 may filter the first pseudo-labels on the basis of learning, and may use a filtering method that uses a research disclosed in, for example, Visual Semantic Reasoning for Image-Text Matching/Kunpeng Li, Yulun Zhang, Kai Li, Yuanyuan Li, and Yun Fu, Department of Electrical and Computer Engineering, Northeastern University, Boston, MA, Khoury College of Computer Science, Northeastern University, Boston, MA (https://openaccess.thecvf.com/content_ICCV_2019/papers/Li_Visual_Semantic_Reasoning_for_Image-Text_Matching_ICCV_2019-paper.pdf). In this case, the filtering processing unit 28 is provided with an image and a text, outputs a plurality of bounding boxes from the image, and matches the bounding boxes with the text to associate the bounding boxes with corresponding positions. Accordingly, the filtering processing unit 28 can filter the bounding boxes that are not associated with the text.

FIG. 3 shows first information I1 that is acquired by the image recognition unit 24, second information I2 that is acquired by the text analysis unit 26, and a first label L2 that is an output of the filtering processing unit 28.

The bounding box B2 different from at least one of the first information I1 or the second information I2 is deleted, so that the first label L2 shown in FIG. 3 includes only the bounding box B1.

The first label L2 and the CT image P1, which are obtained in this way, serve as the training data set that is generated by the information processing apparatus 10.

Here, the filtering processing unit 28 deletes the bounding box B2, which is different from at least one of the first information or the second information, from the first pseudo-label L1. However, in a case where the first pseudo-label L1 includes a bounding box different from at least one of the first information or the second information, the first pseudo-label L1 and the CT image P1 having no label from which the first pseudo-label L1 is output may not be employed as training data.

Since the amount of training data for the first learning model 22 is small, the accuracy of the first learning model 22 is not high. For this reason, there is a possibility that the first learning model 22 provides pseudo-labels to portions other than lesion regions. According to the first embodiment, since the first pseudo-labels are filtered using the first information and the second information, the accuracy of the first pseudo-label can be relatively improved. As a result, training data with high accuracy can be generated. Therefore, in a case where the first pseudo-label having been subjected to the filtering (first label) is used in a training data set, the performance of the learning model can be improved as compared to a case where a training data set using a first pseudo-label not yet subjected to filtering is used.

Second Embodiment

Figure 4:
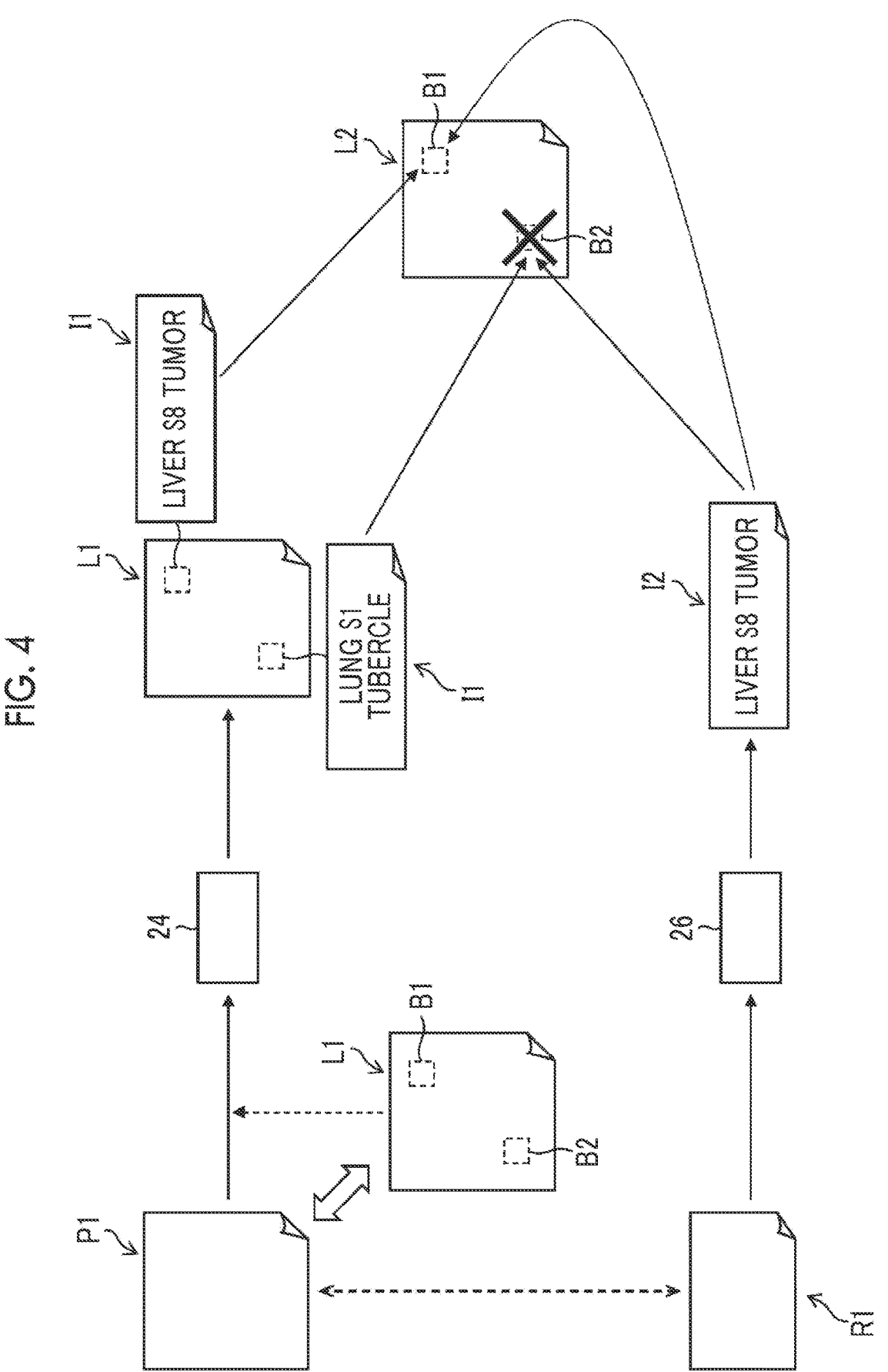
FIG. 4 is a diagram showing details of data processing of a learning method.

FIG. 4 is a diagram showing details of data processing of a learning method. Portions common to FIG. 3 are denoted by the same reference numerals as those in FIG. 3, and the detailed description thereof will be omitted.

The first information I1 is an output of the image recognition unit 24 to which the CT image P1 is input. The first information I1 is added to each of the bounding boxes B1 and B2. In an example shown in FIG. 4, information of "liver S8 tumor" is added to a region of the bounding box B1 and information of "lung S1 tubercle" is added to a region of the bounding box B2. Here, "S8" of "liver S8 tumor" denotes an area of the liver, and "S1" of "lung S1 tubercle" is added to an area of the lung. Here, the area is a small region in a case where the entire one organ is divided into several regions. That is, each of the liver and the lung includes a plurality of preset regions, S8 is one region included in all the regions of the liver, and S1 is one region included in all the regions of the lung.

The second information I2 is an output of the text analysis unit 26 to which the image reading report R1 is input. For example, in a case where "there is a hemangioma in S8" is described in the image reading report R1, the text analysis unit 26 acquires "S8 hemangioma" as the second information I2. In the example shown in FIG. 4, the second information I2 includes "liver S8 tumor".

The bounding box B2 different from at least one of the first information I1 or the second information I2 is deleted from the first pseudo-label L1, so that the first label L2 includes only the bounding box B1. Here, since the information of "liver S8 tumor" of the region of the bounding box B1 matches the information of "liver S8 tumor" of the second information I2, the information of "liver S8 tumor" is employed as a correct label. On the other hand, the information of "lung S1 tubercle" of the region of the bounding box B2 is different from the information of "liver S8 tumor" of the second information I2. For this reason, the information of "lung S1 tubercle" of the bounding box B2 is determined as an incorrect label and is deleted.

The first label L2 and the CT image P1 obtained in this way serve as the training data set.

In a case where "no abnormality" is described in the image reading report R1, the text analysis unit 26 acquires "no abnormality" as the second information I2. In this case, the filtering processing unit 28 deletes the bounding box B1 and the bounding box B2.

Third Embodiment: Learning Method

Figure 5:
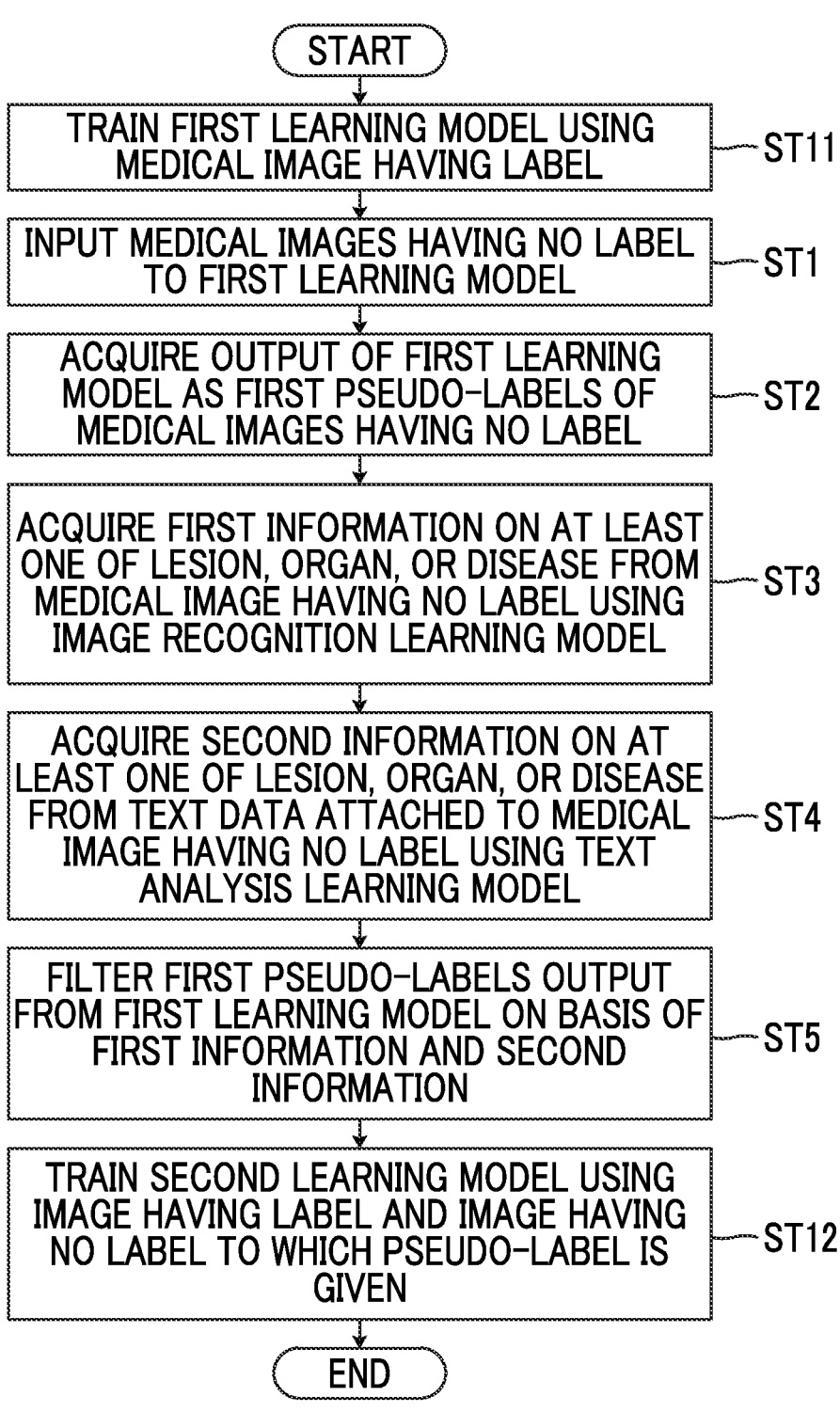
FIG. 5 is a flowchart showing the respective steps of the learning method.

FIG. 5 is a flowchart showing the respective steps of a learning method that is performed by the information processing apparatus 10. Portions common to the flowchart shown in FIG. 3 are denoted by the same reference numerals as those in FIG. 3, and the detailed description thereof will be omitted.

In Step ST11, the processor 12 trains the first learning model 22 using a CT image having a correct answer label. The CT image having a correct answer label is data in which a bounding box is given to a region-of-interest, such as a lesion. Here, the processor 12 inputs a training data set (correct answer data set), which is formed of a CT image having a correct answer label acquired by the image/text acquisition unit 20 and a correct answer label of the CT image, to the first learning model 22 and trains the first learning model 22.

For example, the processor 12 comprises a loss value calculation unit (not shown) and a parameter controller (not shown). In a case where the CT image having a correct answer label of the training data set is input, the processor 12 calculates a loss value between the first pseudo-label output from the first learning model 22 and the correct answer label of the training data set. The processor 12 adjusts parameters of the first learning model 22 to maximize a similarity between the first pseudo-label output from the first learning model 22 and the correct answer label using a backpropagation method on the basis of the calculated loss value.

Subsequently, via the processing of the same steps ST1 to ST5 as those of the first embodiment, the first pseudo-labels output from the first learning model 22 are filtered using the first information and the second information and training data, which is a pair of the CT image having no label and the first label, is generated.

Finally, in Step ST12, the learning device 18 trains the second learning model 30 using a pair of the image having a correct answer label used in Step ST11 and the correct answer label as a training data set. In addition, the learning device 18 trains the second learning model 30 using a pair of the CT image having no label acquired in Step ST1 and the first label (the first pseudo-label having been subjected to the filtering in Step ST5) as a training data set. In a case where only a CT image including a lesion is used to train the second learning model 30 and a first label of the CT image does not include a bounding box indicating the lesion, the CT image is not used to train the second learning model 30.

Here, the learning device 18 trains the second learning model 30 from scratches (from weights initialized with random numbers) using a CNN model having the same structure (the number of layers, the number of parameters) as the first learning model 22. The structure of the second learning model 30 may be different from the structure of the first learning model 22. After the parameters of the first learning model 22 are taken over, the training of the second learning model 30 may be performed again or finely tuned. Further, the parameters of the first learning model 22 may be indirectly used in the training of the second learning model 30. For example, an average value of parameters of a plurality of layers of the first learning model 22 may be taken over as a parameter of one layer of the second learning model 30.

Further, the processing of Step ST12 may be performed after a lot of training data sets are acquired from the repetition of the processing of Steps ST1 to ST5.

Various variations of a method of utilizing the first pseudo-labels and a method of initializing the second learning model 30 are conceivable. For example, as disclosed in US2020/0134427A, an output distribution of the first learning model 22 can also be used as the first pseudo-label. The same applies to a confidence degree. The first learning model 22 can also be trained without using data having labels.

A medical image having no label to which a correct answer label is not given is easily obtained. Further, an image reading report attached to a medical image is easily obtained. Since the amount of training data for the first learning model 22 is small, the accuracy of the first pseudo-labels output from the first learning model 22 is relatively low. However, according to the present embodiment, the accuracy of a label having been subjected to the filtering is relatively improved since the first pseudo-labels are filtered. Accordingly, since a lot of medical images can be used as training data by the training data generation device 16, the learning device 18 can improve the performance of the learning model using training data with high accuracy.

Fourth Embodiment

Figure 6:
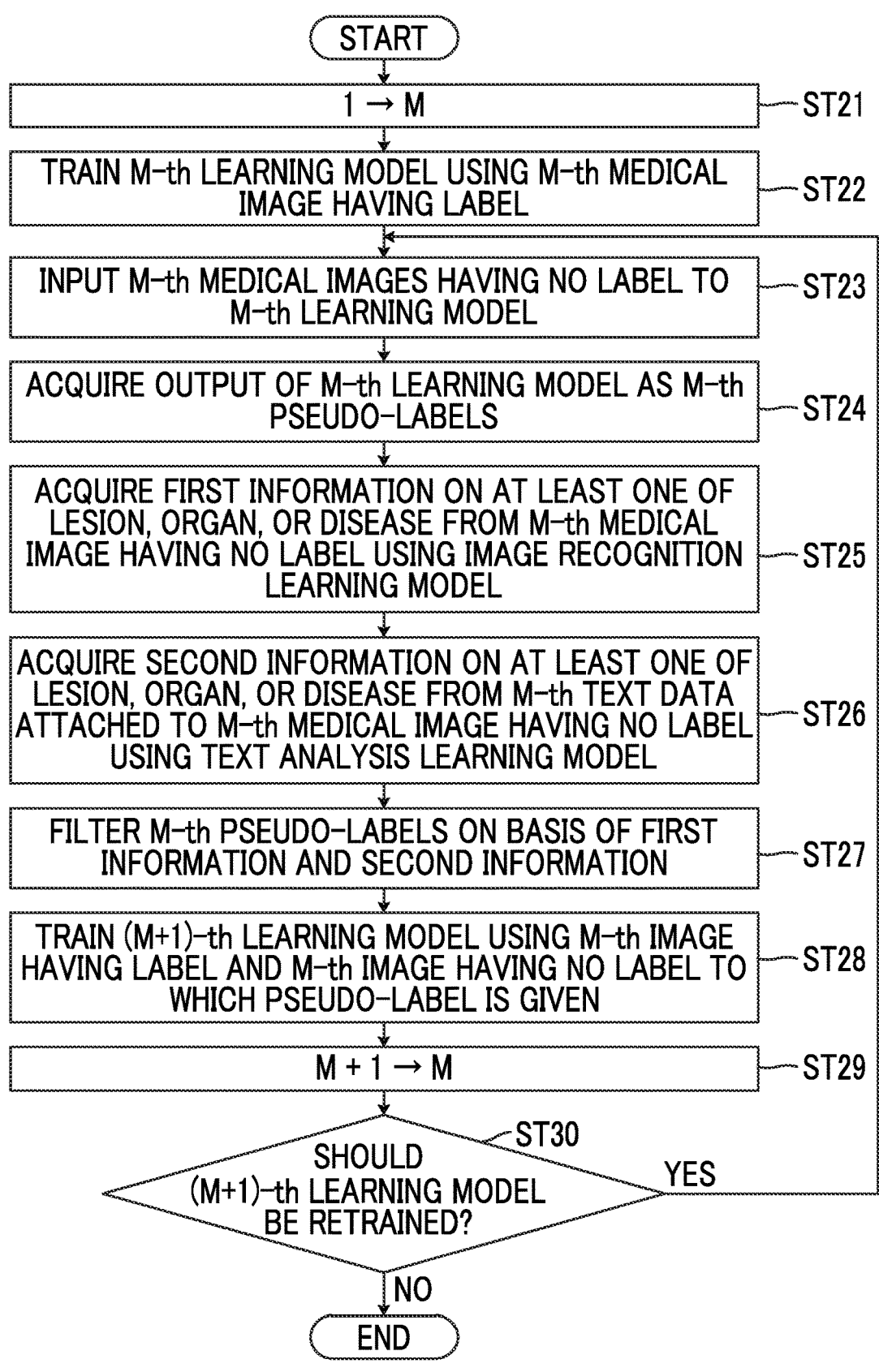
FIG. 6 is a flowchart showing the respective steps of a learning method.

A plurality of learning models can also be repeatedly trained. FIG. 6 is a flowchart showing the respective steps of a learning method that is performed by the information processing apparatus 10. In the third embodiment, the second learning model 30 of the learning device 18 is trained using the first learning model 22 of the training data generation device 16. Meanwhile, although not shown in a fourth embodiment, the (M+1)-th learning model of the learning device 18 is trained using the M-th learning model of the training data generation device 16 in a case where M is an integer. Then, higher-order learning models are sequentially trained as the variable M is increased.

In Step ST21, the processor 12 substitutes the variable M with 1. That is, an initial value of the variable M is set to 1.

In Step ST22, the processor 12 trains the M-th learning model using the M-th medical image having a label.

In Step ST23, the image/text acquisition unit 20 acquires the M-th medical images having no label (an example of "the M-th images having no label") and the M-th image reading reports (an example of "the M-th texts") that are attached to the M-th medical images having no label. The image/text acquisition unit 20 inputs the M-th medical images having no label to the M-th learning model trained in Step ST22. The M-th learning model outputs bounding boxes to the positions of lesion regions of the input M-th medical images. In Step ST24, the processor 12 acquires an output of the M-th learning model as the M-th pseudo-labels of the M-th medical images having no label.

In Step ST25, the image recognition unit 24 inputs the M-th medical image having no label to the image recognition learning model 24A and acquires first information on at least one of the position of a lesion, an organ name, or a disease name from the M-th medical image having no label.

In Step ST26, the text analysis unit 26 inputs a text of the M-th image reading report of the M-th medical image having no label to the text analysis learning model 26A, and acquires second information on at least one of the position of the lesion in the M-th medical image having no label, an organ name, or a disease name from the text.

In Step ST27, the filtering processing unit 28 filters the M-th pseudo-labels acquired in Step ST24 on the basis of the first information of the M-th image having no label acquired in Step ST25 and the second information of the M-th image having no label acquired in Step ST26, and acquires the M-th label that is the M-th pseudo-label having been subjected to the filtering.

In Step ST28, the learning device 18 trains the (M+1)-th learning model using the M-th medical image having a label used in Step ST22. In addition, the learning device 18 trains the (M+1)-th learning model using the M-th medical image having no label acquired in Step ST23 and the M-th pseudo-label having been subjected to the filtering in Step ST27 as a training data set. The processing of Step ST28 may be performed after a lot of training data sets are acquired from the repetition of the processing of Steps ST23 to ST27.

In Step ST29, the processor 12 adds 1 to the variable M.

In Step ST30, the processor 12 determines whether or not to retrain the M-th learning model. For example, the processor 12 determines whether or not the variable M exceeds N that is an integer of 2 or more. That is, the processor 12 repeatedly retrains the M-th learning model until the number of times of the processing of Steps ST23 to ST28 reaches N. In a case where the processor 12 retrains the M-th learning model, the processor 12 returns to Step ST23 and repeats the same processing. In a case where the processor 12 does not retrain the M-th learning model, the processor 12 ends the processing of this flowchart.

As described above, the M-th pseudo-labels that are the output of the M-th learning model are filtered to acquire the M-th label and the (M+1)-th learning model is trained using the M-th label to repeatedly increase M, so that a learning model with high accuracy can be finally generated.

The M-th pseudo-labels of the M-th medical images having no label, which are input in Step ST23 and to which bounding boxes are not given in Step ST24, cannot be not filtered in Step ST27, and the M-th medical images having no label cannot be used as training data in Step ST28. However, in a case where the accuracy of a higher-order learning model is improved, the M-th pseudo-label can be output even though such medical images having no label are input.

[Others]

The first information on the state of the subject is information on a disease name in the above-mentioned embodiments, but the first information on the state of the subject may be information on the extent of a disease. For example, the extent of a disease may be information that indicates any of severe, moderate, and a mild disease.

Further, an example in which training data for a medical image is generated has been described in the above-mentioned embodiments, but an image handled by the information processing apparatus 10 is not limited to a medical image. That is, first information on at least one of the region, type, or state of a subject of an image having no label may be acquired from the image having no label, and second information on at least one of the region, type, or state of the subject of the image having no label may be acquired from sentence information attached to the image having no label.

Furthermore, the bounding box indicating a lesion region has been described as an example of the pseudo-label, but the bounding box may indicate the type of a lesion. For example, the pseudo-label may be a bounding box that indicates a tumor and a tubercle with different colors.

Further, the pseudo-label is not limited to a bounding box. For example, the pseudo-label may be segmentation indicating existence probability, may be instance segmentation, or may be a result in which a segmentation result is converted into a bounding box. The segmentation may be segmentation showing a lesion and a portion other than the lesion, or may be segmentation in which even the type of a lesion is classified.

The technical scope of the present invention is not limited to the range described in the above-described embodiments. The configurations and the like of the respective embodiments can be appropriately combined between the respective embodiments without departing from the scope of the present invention.

EXPLANATION OF REFERENCES

10: information processing apparatus
12: processor
14: memory
16: training data generation device
18: learning device
20: image/text acquisition unit
22: first learning model
24: image recognition unit
24A: image recognition learning model
26: text analysis unit
26A: text analysis learning model
28: filtering processing unit
30: second learning model
B1: bounding box
B2: bounding box
I1: first information
I2: second information
L1: first pseudo-label
L2: first label
P1: CT image
R1: image reading report
ST1 to ST5: each step of training data generation method
ST11, ST12, ST21 to ST30: each step of learning method

What is claimed is:

1. A training data generation device comprising:
at least one processor; and
at least one memory that stores a command to be executed by the at least one processor,
wherein the at least one processor
acquires first images having no label and first texts attached to the first images having no label,
inputs the first image to an image recognition learning model and acquires an output of the image recognition learning model as first information on at least one of a region, a type, or a state of a subject of the first image having no label from the first image having no label,
inputs the first text to a text analysis learning model and acquires an output of the text analysis learning model as second information on at least one of a region, a type, or a state of the subject of the first image having no label from the first text,
inputs the first images having no label to a first learning model, which outputs a label relating to a region-of-interest of an image in a case where the image is input, and acquires an output of the first learning model as first pseudo-labels of the first images having no label, and
filters the first pseudo-labels by deleting information included in the first pseudo-labels that is different from at least one of the first information or the second information.

2. The training data generation device according to claim 1,
wherein the first image having no label is a medical image, and
the region, the type, and the state of the subject are a position of a lesion, an organ name, and a disease name, respectively.

3. A learning device comprising:
the training data generation device according to claim 1,
wherein the at least one processor trains the first learning model using an image having a label and a label of the image having a label as training data, and trains a second learning model, which outputs a label relating to a region-of-interest of the image in a case where the image is input, using the first image having no label and a first label that is the first pseudo-label having been subjected to the filtering as training data.

4. The learning device according to claim 3, wherein the first learning model and the second learning model include convolutional neural networks.

5. The learning device according to claim 4, wherein the first learning model and the second learning model include convolutional neural networks having the same configuration.

6. The learning device according to claim 3, wherein in a case where an initial value of M as a variable is set to 1 and N is an integer of 2 or more, the at least one processor repeats processing the N times, the processing including acquiring M-th images having no label and M-th texts attached to the M-th images having no label, acquiring the first information on at least one of a region, a type, or a state of a subject of the M-th image having no label from the M-th image having no label, acquiring the second information on at least one of a region, a type, or a state of the subject of the M-th image having no label from the M-th text, inputting the M-th images having no label to a M-th learning model and acquires an output of the M-th learning model as M-th pseudo-labels, filtering the M-th pseudo-labels on the basis of the first information and the second information of the M-th image having no label, training a (M+1)-th learning model, which outputs a label relating to a region-of-interest of the image in a case where the image is input, using the M-th image having no label and the first label that is the M-th pseudo-label having been subjected to the filtering as training data, and adding 1 to the M.

7. A training data generation method comprising:

an image acquisition step of acquiring first images having no label and first texts attached to the first images having no label;

a first information acquisition step of inputting the first image to an image recognition learning model and acquiring an output of the image recognition learning model as first information on at least one of a region, a type, or a state of a subject of the first image having no label from the first image having no label;

a second information acquisition step of inputting the first text to a text analysis learning model and acquiring an output of the text analysis learning model as second information on at least one of a region, a type, or a state of the subject of the first image having no label from the first text;

a pseudo-label acquisition step of inputting the first images having no label to a first learning model, which outputs a label relating to a region-of-interest of an image in a case where the image is input, and acquiring an output of the first learning model as first pseudo-labels of the first images having no label; and a filtering step of filtering the first pseudo-labels by deleting information included in the first pseudo-labels that is different from at least one of the first information or the second information.

8. A non-transitory, computer-readable tangible recording medium which records thereon a program that causes, when read by a computer, the computer to execute the training data generation method according to claim 7.

\* \* \* \* \*